US010363846B2

(12) United States Patent
Gallagher et al.

(10) Patent No.: US 10,363,846 B2
(45) Date of Patent: Jul. 30, 2019

(54) VEHICLE SEATING SYSTEM HAVING SEAT WITH INDIVIDUALLY CONTROLLABLE ELECTROMAGNETIC COILS

(71) Applicant: Lear Corporation, Southfield, MI (US)

(72) Inventors: David Gallagher, Sterling Heights, MI (US); Francesco Migneco, Salene, MI (US)

(73) Assignee: Lear Corporation, Southfield, MI (US)

( * ) Notice: Subject to any disclaimer, the term of this patent is extended or adjusted under 35 U.S.C. 154(b) by 277 days.

(21) Appl. No.: 15/607,797

(22) Filed: May 30, 2017

(65) Prior Publication Data

US 2018/0345833 A1 Dec. 6, 2018

(51) Int. Cl.
*B60N 2/56* (2006.01)
*A61N 2/02* (2006.01)
(Continued)

(52) U.S. Cl.
CPC ........ *B60N 2/5678* (2013.01); *A61B 5/04004* (2013.01); *A61B 5/1036* (2013.01); *A61B 5/1114* (2013.01); *A61B 5/1116* (2013.01); *A61B 5/4848* (2013.01); *A61B 5/6893* (2013.01); *A61N 2/02* (2013.01); *G05D 23/015* (2013.01); *G05D 23/24* (2013.01); *G05D 23/303* (2013.01); *A61B 5/0077* (2013.01); *A61B 5/1118* (2013.01); *A61B 5/1128* (2013.01); *A61B 2503/22* (2013.01); *A61B 2562/0204* (2013.01); *A61B 2562/0219* (2013.01);
(Continued)

(58) Field of Classification Search
CPC ...... A61N 2/00–12; B60N 2/00; B60N 2/002; B60N 2/24; B60N 2/5678; B60N 2/64; B60N 2/663; B60N 2/665; B60N 2/80; B60N 2/90; B60N 2/976
See application file for complete search history.

(56) References Cited

U.S. PATENT DOCUMENTS 5,817,000 A 10/1998 Souder
6,418,345 B1 * 7/2002 Tepper .................... A61N 2/02
600/14
(Continued)

FOREIGN PATENT DOCUMENTS

CN 2855822 Y 1/2007
CN 203186154 U 9/2013
(Continued)

OTHER PUBLICATIONS

German Patent and Trademark Office, Office Action for the corresponding German Patent Application No. 10 2018 201 760.3 dated Feb. 14, 2019.

*Primary Examiner* — Thaddeus B Cox
(74) *Attorney, Agent, or Firm* — Brooks Kushman P.C.

(57) ABSTRACT

A seating system for a vehicle includes a vehicle seat, individually selectable and controllable electromagnetic coils individually positioned at respective locations within the seat corresponding to anatomical locations of a person sitting in the vehicle seat, and a controller. The electromagnetic coils to generate electromagnetic fields when activated. The controller to individually activate a subset of the electromagnetic coils to deliver electromagnetic energy to the anatomical locations of the person corresponding to the respective locations within the vehicle seat of the activated electromagnetic coils.

18 Claims, 4 Drawing Sheets

(51) Int. Cl.
  *G05D 23/24* (2006.01)
  *G05D 23/01* (2006.01)
  *G05D 23/30* (2006.01)
  *A61B 5/04* (2006.01)
  *A61B 5/103* (2006.01)
  *A61B 5/00* (2006.01)
  *A61B 5/11* (2006.01)
  *G05D 27/02* (2006.01)

(52) U.S. Cl.
  CPC ............... *A61B 2562/0247* (2013.01); *A61B 2562/0257* (2013.01); *G05D 27/02* (2013.01)

(56) References Cited

U.S. PATENT DOCUMENTS

| | | |
|---|---|---|
| 6,500,110 B1 | 12/2002 | Davey et al. |
| 6,506,153 B1 | 1/2003 | Littek et al. |
| 6,682,494 B1 | 1/2004 | Sleichter, III et al. |
| 7,219,923 B2 | 5/2007 | Fujita et al. |
| 7,326,170 B1 | 2/2008 | Miller |
| 7,650,192 B2 | 1/2010 | Wahlstrand |
| 7,678,041 B2 | 3/2010 | Prenzel et al. |
| 7,731,279 B2 | 6/2010 | Asada et al. |
| 7,808,395 B2 | 10/2010 | Raisanen et al. |
| 8,706,204 B2 | 4/2014 | Seo et al. |
| 8,710,784 B2 | 4/2014 | Meyer et al. |
| 8,725,311 B1 | 5/2014 | Breed |
| 8,971,839 B2 | 3/2015 | Hong |
| 8,979,191 B2 | 3/2015 | Friderich et al. |
| 8,989,697 B2 | 3/2015 | Leung et al. |
| 9,237,242 B2 | 1/2016 | Basir |
| 9,272,689 B2 | 3/2016 | Fung et al. |
| 9,277,385 B2 | 3/2016 | Iwamoto |
| 2004/0119599 A1 | 6/2004 | Stevenson et al. |
| 2006/0145457 A1 | 7/2006 | Prenzel et al. |
| 2014/0024882 A1* | 1/2014 | Chornenky ............ A61N 1/40 600/14 |
| 2015/0266405 A1 | 9/2015 | Fitzpatrick et al. |
| 2016/0278709 A1 | 9/2016 | Ridao Granado et al. |

FOREIGN PATENT DOCUMENTS

| | | |
|---|---|---|
| CN | 102975642 B * | 12/2015 |
| DE | 4014334 A1 | 11/1991 |
| DE | 202005009460 U1 | 9/2005 |
| DE | 102004058722 A1 | 6/2006 |
| DE | 102006029293 A1 | 12/2007 |
| DE | 202009013768 U1 | 2/2011 |
| DE | 102014218744 A1 | 3/2016 |
| EP | 2308559 A2 | 4/2011 |
| JP | 2005247097 A * | 9/2005 |
| WO | 2015127193 A1 | 8/2015 |
| WO | 2016099299 A1 | 6/2016 |

* cited by examiner ent invention relates to electromagnetic field
VEHICLE SEATING SYSTEM HAVING SEAT WITH INDIVIDUALLY CONTROLLABLE ELECTROMAGNETIC COILS

TECHNICAL FIELD

The present invention relates to electromagnetic field stimulation of a person in a vehicle environment.

BACKGROUND

Localized musculo-skeletal discomfort such as lower back pain is a common affliction in the general population. Electromagnetic field stimulation may provide a significant therapeutic benefit and may be more effective than over-the-counter pain medications in the treatment of pain and discomfort, with overall longer lasting effects.

Being positioned inside a confined environment such as within a vehicle, with a limited range of movement and increased pressure and force placed upon various areas, can worsen pre-existing discomfort and pain. A person has a limited range of movement while being in a vehicle. This "locked position" may induce muscle spasms and subsequent pain. At this point, a pain-spasm-pain cycle is triggered, making the situation worse as the number of driven hours increases.

Reducing discomfort increases the person's overall health by relieving stress. In the case of the person being the driver of the vehicle, reducing discomfort also decreases driver distraction caused by the discomfort. Therefore, the driver can focus attention on safe vehicle operation.

SUMMARY

In an embodiment, a seating system for a vehicle is provided. The seating system includes a vehicle seat, individually selectable and controllable electromagnetic coils individually positioned at respective locations within the seat corresponding to anatomical locations of a person sitting in the seat, and a controller. The electromagnetic coils to generate electromagnetic fields when activated. The controller to individually activate a subset of the electromagnetic coils to deliver electromagnetic energy to the anatomical locations of the person corresponding to the respective locations within the seat of the activated electromagnetic coils.

The seating system may further include a human-machine interface to receive from the person a selection of the electromagnetic coils to activate. The controller to individually activate the electromagnetic coils selected by the person.

The seating system may further include a biometric sensor to detect locations of discomfort of the person. The controller to individually activate the electromagnetic coils in accordance with a suggested treatment plan based on the detected locations of discomfort of the person. The biometric sensor may include at least one of a EMG-based device, a localized oxygen level detector, and a pressure detector.

The seating system may further include a fidget sensor to detect locations of fidgeting of the person. The controller to individually activate the electromagnetic coils in accordance with a suggested treatment plan based on the detected locations of fidgeting of the person. The fidget sensor may include at least one of a piezo-electric sensor, a radar sensor, a Doppler based sensor, a piezo-resistive sensor, a capacitive sensor, a pressure-based sensor, and a camera.

The electromagnetic coils may include sewn conductive fibers.

The electromagnetic coils may be integrated into sub-components of the seat, between trim components and foam components of the seat, or part of an independent structure separately removable from the seat.

The seating system may further include a current generator to generate electrical currents. The controller to control electrical currents supplied from the current generator to the subset of the electromagnetic coils to individually activate the subset of the electromagnetic coils.

The seating system may further include air bladders disposed within the seat. At least some of the electromagnetic coils are respectively positioned against at least some of the bladders. The controller may control inflating and deflating of the bladders having the activated electromagnetic coils positioned thereon in conjunction with activating the activated electromagnetic coils.

In an embodiment, another seating system for a vehicle is provided. The seating system includes a vehicle seat, individually selectable and controllable electromagnetic coils individually positioned at respective locations within the seat corresponding to anatomical locations of a person sitting in the seat, a current generator, and a controller. The current generator to generate electrical currents. The electromagnetic coils to generate electromagnetic fields having characteristics in correspondence with characteristics of electrical currents supplied to the electromagnetic coils. The controller to individually activate a subset of the electromagnetic coils and control electrical currents supplied from the current generator to the activated electromagnetic coils for the activated electromagnetic coils to deliver electromagnetic energy in correspondence with the electrical currents to the anatomical locations of the person corresponding to the respective locations within the seat of the activated electromagnetic coils.

The seating system may further include a human-machine interface and the controller may be programmed with one or more treatment plans each having unique electromagnetic coil activation and electromagnetic field characteristics settings. The human-machine interface to receive from the person a selection of one of the treatment plans. The controller to individually activate the electromagnetic coils and control the electrical currents supplied from the current generator to the activated electromagnetic coils in accordance with the selected treatment plan.

The seating system may further include a biometric sensor to detect locations of discomfort of the person. The controller to individually activate the electromagnetic coils and control the electrical currents supplied from the current generator to the activated electromagnetic coils in accordance with a suggested treatment plan based on the detected locations of discomfort of the person.

The seating system may further include a fidget sensor to detect locations of fidgeting of the person. The controller to individually activate the electromagnetic coils and control the electrical currents supplied from the current generator to the activated electromagnetic coils in accordance with a suggested treatment plan based on the detected locations of fidgeting of the person.

The seating system may further include air bladders disposed within the seat. At least some of the electromagnetic coils are respectively positioned against at least some of the bladders. The controller to control inflating and deflating of the bladders having the activated electromagnetic coils positioned thereon in conjunction with activating the activated electromagnetic coils and controlling the electrical currents supplied from the current generator to the activated electromagnetic coils.

The seating system may further include a biometric sensor to detect locations of discomfort of the person. The controller to individually activate the electromagnetic coils, control the electrical currents supplied from the current generator to the activated electromagnetic coils, and control inflating and deflating of the bladders having the activated electromagnetic coils positioned thereon in accordance with a suggested treatment plan based on the detected locations of discomfort of the person.

The seating system may further include a fidget sensor to detect locations of fidgeting of the person. The controller to individually activate the electromagnetic coils, control the electrical currents supplied from the current generator to the activated electromagnetic coils, and control inflating and deflating of the bladders having the activated electromagnetic coils positioned thereon in accordance with a suggested treatment plan based on the detected locations of fidgeting of the person.

DETAILED DESCRIPTION

Detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
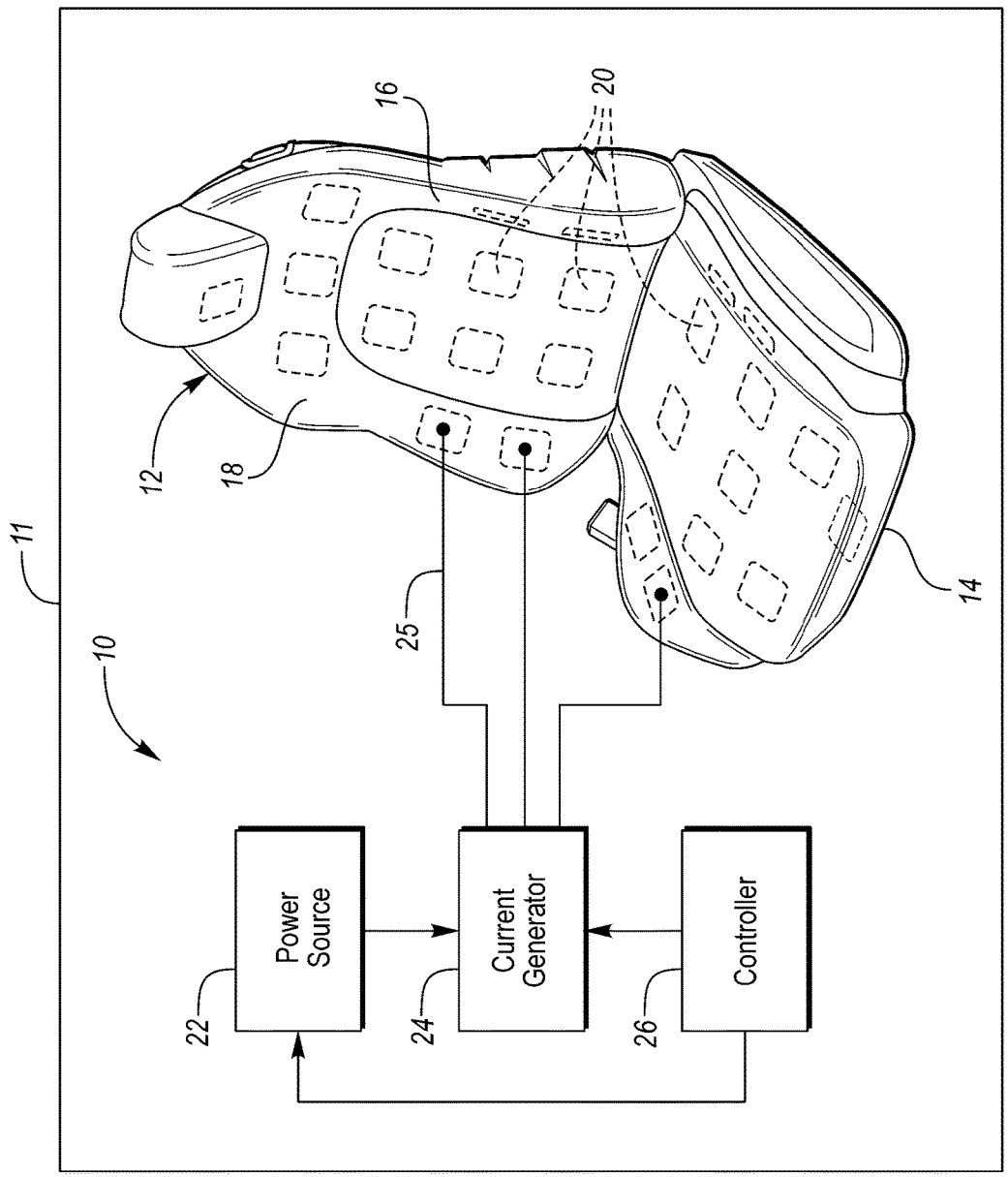
FIG. 1 illustrates a perspective view of a seating system for a vehicle including a perspective view of a vehicle seat of the seating system and a block diagram of other components of the seating system.

Referring now to FIG. 1, a vehicle seating system 10 will be described. Seating system 10 is implemented in a vehicle 11. Vehicle 11 may be a car, truck, or the like. Seating system 10 includes a seat 12. A perspective view of seat 12 is shown in FIG. 1. Seat 12 includes a seat bottom (i.e., a seat cushion) 14 and a seat back 16. Seat bottom 14 is configured to support the sitting region of a person sitting in seat 12. Seat back 16 is configured to support the back of the person sitting in seat 12. Seat back 16 is pivotably connected to seat bottom 14 to extend upright relative to the seat bottom. Seat 12 further includes a cover 18 which covers or upholsters seat bottom 14 and seat back 16.

Seating system 10 is designed to deliver localized electromagnetic energy from individually selectable areas of seat 12 to a person sitting in the seat. Seating system 10 in operation delivers electromagnetic energy targeted to affected anatomical areas of the person. An intended use of the targeted electromagnetic energy is for the treatment of the person's localized pain and discomfort resulting from musculo-skeletal afflictions.

As shown in in phantom in FIG. 1, seat 12 includes an array of electromagnetic coils 20. Electromagnetic coils 20 are configured to generate electromagnetic fields when activated. Electromagnetic coils 20 are distributed across seat bottom 14 and seat back 16. Seat bottom 14 and seat back 16 are divided into any number of electromagnetic coils 20 based on the seat design.

More particularly, electromagnetic coils 20 are strategically arranged within seat 12 to correspond with general anatomical locations of major muscle groups of a person sitting in the seat. Electromagnetic coils 20 work independently of one another via a master controller such that they can function alone or in unison to provide localized electromagnetic energy stimulation. As such, electromagnetic coils 20 are individually selectable and controllable to generate electromagnetic fields. Electromagnetic coils 20 in different areas of seat 12 can be selected individually or in any combination to deliver electromagnetic energy to affected anatomical areas of concern of an occupant of the seat. In this way, each area of seat 12 can be selected individually or in any combination to match affected anatomical areas of concern of a person sitting in the seat.

Electromagnetic coils 20 can be made of various materials and shapes. Electromagnetic coils 20 can be constructed out of traditional wire with either a hollow or solid core. Electromagnetic coils 20 can be manufactured out of conductive fibers sewn or pressed into shape. Electromagnetic coils 20 can be integrated into the seat cushion foam or into the seat trim itself. Electromagnetic coils 20 can exist separately between the foam and trim as stand-alone units. The geometry, placement, and materials of electromagnetic coils 20 depend upon intended use and location. The spatial density of the array of electromagnetic coils 20 can conform to seating design on a case by case basis.

Seating system 10 further includes a power source 22, an electrical current generator 24, and a controller 26. Current generator 24 is configured to generate alternating electrical currents (i.e., AC or time-varying electrical currents). Current generator 24 uses electrical power from power source 22 to generate the currents. Current generator 24 provides the currents to electromagnetic coils 20. Electromagnetic coils 20 generate electromagnetic fields from being driven with the currents. Characteristics (e.g., intensity, frequency, etc.) of the electromagnetic fields generated by electromagnetic coils 20 correspond to characteristics (e.g., amplitude, frequency, etc.) of the currents supplied from current generator 24 to the electromagnetic coils.

Current generator 24 is individually connected to electromagnetic coils 20 via electrical conductors 25. For example, current generator 24 may have a plurality of output ports which are respectively connected by electrical conductors 25 to respective electromagnetic coils 20. As such, current generator 24 is individually connected to electromagnetic coils 20 to provide electrical currents to the electromagnetic coils.

Current generator 24 is configured to generate a plurality of unique electrical currents at any given time. The number of unique currents that current generator 24 can generate at any given time is at least the same number of output ports of the current generator. As such, current generator 24 is operable to provide unique currents respectively to electromagnetic coils 20 at any given time. Consequently, electromagnetic coils 20 generate unique electromagnetic fields in correspondence with the unique currents provided to the electromagnetic coils.

The electrical currents that current generator 24 can generate may have waveform or pulse characteristics. In this way, current generator 24 is a waveform or pulse generator. The uniqueness of a given current from other currents may be from unique waveform or pulse characteristics of the given current.

Controller 26 is configured to control current generator 24 to have the current generator generate the electrical currents for electromagnetic coils 20. Controller 26 provides one or more control signals to current generator 24 for the current generator to generate one or more currents in correspondence with the one or more control signals. The control signals may include information indicative of characteristics (e.g., amplitude, frequency, intensity, strength, duration, continuous vs. pulse, shape, sinusoidal, triangle, vs. square waveform, duration, repetition, etc.) the currents are to have and information indicative of which electromagnetic coils 20 are to receive which currents. The currents may be unique from one another by having different characteristics. That is, the characteristics of the currents may be different from one another whereby the currents are unique from one another.

For example, controller 26 provides to current generator 24 a control signal which includes information indicating that the current generator is to generate an electrical current "A" for all electromagnetic coils 20. Current generator 24 in response to the control signal generates and provides the current "A" to all electromagnetic coils 20. In turn, each electromagnetic coil 20 generates an electromagnetic field in correspondence with being driven by the current "A".

As another example, controller 26 provides current generator 24 with a first control signal which includes information indicating that the current generator is to generate an electrical current "A" for a first one of electromagnetic coils 20 and provides the current generator with a second control signal which includes information indicating that the current generator is to generate an electrical current "B" for a second one of electromagnetic coils 20. Current generator 24 in response to the first and second control signals generates and provides the current "A" to the first one of electromagnetic coils 20 and generates and provides the current "B" to the second one of electromagnetic coils 20. In turn, the first one of electromagnetic coils 20 generates an electromagnetic field in correspondence with being driven by the current "A" and the second one of electromagnetic coils 20 generates an electromagnetic field in correspondence with being driven by the current "B".

In sum, controller 26 is configured to provide unique control signals to current generator 24. Current generator 24 generates unique electrical currents in correspondence with the control signals and provides the currents to selected ones of electromagnetic coils 20. The selected ones of electromagnetic coils 20 generate electromagnetic fields in correspondence with the unique currents provided to the selected ones of the electromagnetic coils. In this way, electromagnetic coils 20 are each adjustable and can be individually or collectively powered to generate electromagnetic fields. Controller 26 may also control power source 22 to control the electrical power supplied from the power source to current generator 24.

As described, seating system 10 provides a time-varying electromagnetic field stimulation system in vehicle seating designed to penetrate soft tissue and joints of the person sitting in seat 12 to increase mobility and/or reduce pain and discomfort of the affected anatomical areas of the person. Seat cushion 14 and seat back 16 are populated with electromagnetic coils 20. Electromagnetic coils 20, per the properties of electromagnetism, produce electromagnetic fields when (alternating or time-varying) electrical currents are applied to the electromagnetic coils. The electromagnetic fields penetrate soft tissue and/or joints of the person sitting in seat 12. Rapidly changing electromagnetic field pulses induce a physiological response in the application area of the person sitting in seat 12. Current generator 24 and controller 26 in conjunction can control electromagnetic coils 20 to vary the electromagnetic field pulsation frequency, duration, sequence, etc., to target specific types of stimulation and effects. The array of electromagnetic coils 20 can be strategically positioned on seat 12 and independently controlled to produce unique electromagnetic field shapes and strengths at the surface of the seat.

Figure 2:
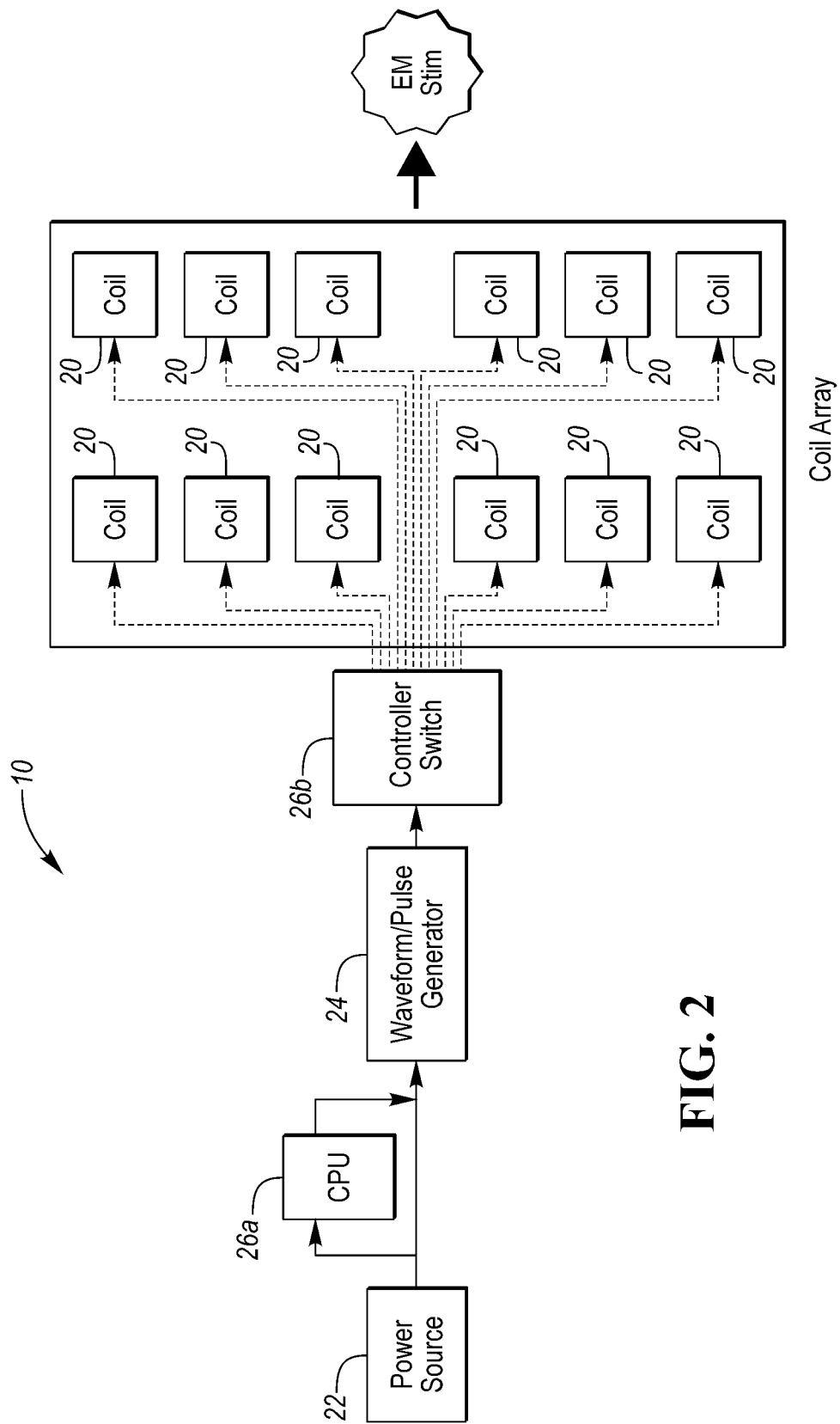
FIG. 2 illustrates a functional block diagram of the seating system.

Referring now to FIG. 2, with continual reference to FIG. 1, a functional block diagram of seating system 10 is shown. Controller 26 is represented in FIG. 2 as having a central processor unit (CPU) 26a and a controller switch 26b. CPU 26a is in-line with power source 22. CPU 26a selects a unique pulse sequence signal (i.e., a unique control signal) to be applied based on pre-programmed or selected designs. The pulse sequence signal is provided to current generator 24 (labeled "waveform/pulse generator" in FIG. 2). Current generator 24 transforms the pulse sequence signal into a physical electrical current pulse sequence. The electrical current pulse sequence is provided from current generator 24 to controller switch 26b. Controller switch 26b multiples the electrical current pulse sequence by the number of electromagnetic coils 20 selected either by the person sitting in seat 12 or by a pre-programmed arrangement. That is, controller switch 26b splits the electrical current pulse sequence into copies of the electrical current pulse sequence and transfers a respective copy to a respective electromagnetic coil 20 to be activated. In pre-programmed therapies the electrical current pulse sequence can also be multiplied by a field strength coefficient fx to vary the strength across individual electromagnetic coils 20 as well. The electrical current pulse sequence in an electromagnetic coil 20 generates a proportional magnetic field that permeates and stimulates the affected areas of the person sitting in seat 12. A timer in CPU 26a controls the duration of the treatment and the minimum period between successive treatments.

As described, seating system 10 includes an array of electromagnetic coils 20 which are geometrically arranged within the structure of seat 12 to coincide with the body of a person sitting in the seat. Electromagnetic coils 20 generate electromagnetic fields driven by unique electric currents (e.g., electric current pulse sequences) output by current generator 24. Electromagnetic energy of the electromagnetic fields penetrates the soft tissue and joints of the person sitting in seat 12. The rapidly changing electromagnetic fields generate internal electromagnetic responses within the body of the person sitting in seat 12. The internal responses themselves are coded in frequency and intensity by frequency and intensity of the applied electromagnetic fields. Stimuli received and its effects are a result of the unique electrical current pulse sequence selected during treatment. Typical tissue response is perceived as a reduction of pain and increase in mobility of the affected areas of the person sitting in seat 12.

Figure 3:
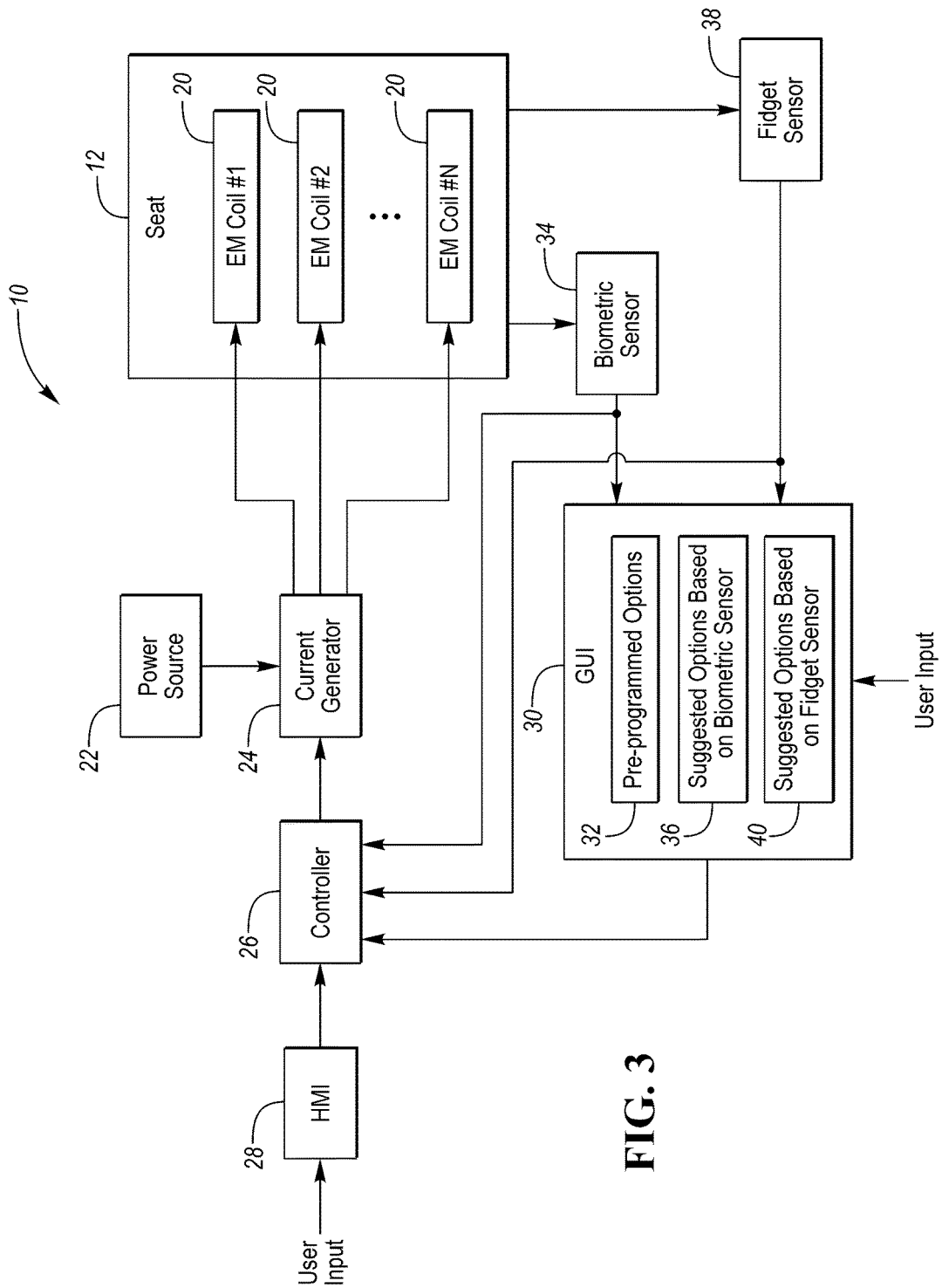
FIG. 3 illustrates a more detailed block diagram of the seating system.

Referring now to FIG. 3, with continual reference to FIGS. 1 and 2, a more detailed block diagram of seating system 10 is shown. As described, electromagnetic coils 20 are controlled by controller 26 which regulates current generator 24. The electrical current distribution from current generator 24 to electromagnetic coils 20 as controlled by controller 26 is manipulated via an input device or the like to activate various ones of the electromagnetic coils. Selection of electromagnetic coils 20 for activation (i.e., location(s) selection of seat 12 for electromagnetic field generation) and electromagnetic field strength settings may be carried out in various ways in seating system 10. One way for activation selection of electromagnetic coils 20 and electromagnetic field characteristics settings involves a user providing manual input to controller 26. In this regard, seating system 10 further includes an input device in the form of a human-machine interface (HMI) device 28 in communication with controller 26. A user such as a person sitting in seat 12 accesses HMI device 28 to provide manual input to controller 26. For instance, HMI device 28 may include a touchscreen, knobs, buttons, microphone for voice commands, etc. The person accesses HMI device 28 to select which electromagnetic coils 20 are to be activated, the electromagnetic field characteristics settings of the electromagnetic coils which are to be activated, the duration of activation, and the like. Controller 26 in turn controls current generator 24 to provide the appropriate electrical currents to selected ones of electromagnetic coils 20 thereby causing electromagnetic energy to be delivered from these electromagnetic coils to the person sitting in seat 12 per the manual input.

In embodiments, seating system 10 may further include a machine learning unit to recognize dynamic user preferences over time. The machine learning unit may generate new user profiles fitting to each user from based on the recognized user preferences. The machine learning unit can be further augmented with objective EEG, heart rate, breathing rate, heart rate variability (HRV) response data to the effectiveness of each user profile.

Another way for activation selection of electromagnetic coils 20 and electromagnetic field characteristics settings involves pre-programmed treatment plans. Controller 26 may be pre-programmed with one or more treatment plans each having unique selection of electromagnetic coils 20 and electromagnetic field characteristics settings. In general, the pre-programmed treatment plans are suited for specific types of pain management. The pre-programmed treatment plans may be provided from a therapist or the like. The pre-programmed treatment plans are tailorable to different needs of persons who may sit in seat 12 and encompass, at a minimum, electromagnetic energy treatment of cervical, thoracic, lumbar, and sacral areas of the persons.

A user may select one of the pre-programmed treatment plans by accessing an input device in communication with controller 26. In this regard, seating system 10 further includes a graphical user interface (GUI) 30 in communication with controller 26. GUI 30 is configured to display pre-programmed options 32 for a user to view. Pre-programmed options 32 respectively correspond to the pre-programmed treatment plans. The user accesses GUI 30 to select one of the pre-programmed options 32. Controller 26 in turn controls current generator 24 to provide the appropriate electrical currents to selected ones of electromagnetic coils 20 thereby causing electromagnetic energy to be delivered from these electromagnetic coils 20 to the person sitting in seat 12 per the pre-programmed treatment plan corresponding to the selected pre-programmed option 32.

Another way for activation selection of electromagnetic coils 20 and electromagnetic field strength settings involves (i) automatic suggestion by seating system 10 of the electromagnetic coils and electromagnetic field characteristics settings for consideration by the user to select and/or (ii) automatic selection by the seating system of the electromagnetic coils and electromagnetic field characteristics settings. In this regard, seating system 10 further includes one or more biomedical/biometrical systems (not shown) installed in seat 12 and/or in/around the vehicle. Sensor-based inputs from the biomedical/biometric systems to GUI 30 are used for the automatic suggestion of electromagnetic coils 20 and electromagnetic field characteristics settings. Likewise, the sensor-based inputs from the biomedical/biometric systems directly to controller 26 are used for the automatic selection of electromagnetic coils 20 and electromagnetic field characteristics settings.

Biometric sensor 34 shown in FIG. 2 represents the sensor(s) providing the sensor-based inputs from the biomedical/biometrical systems of seating system 10. Biometric sensor 34 is configured to detect the level of discomfort and pain and the location of the affected area(s) of a person sitting in seat 12 and intuitively suggest one or more treatment plans. Biometric sensor 34 is in communication with GUI 30 to provide the suggested treatment plans to the GUI. GUI 30 in turn displays suggested treatment options 36 corresponding to the suggested treatment plans for the person to view. Upon the person selecting one of the suggested treatment options 36, controller 26 controls current generator 24 to provide the appropriate electrical currents to selected ones of electromagnetic coils 20 thereby causing electromagnetic energy to be delivered from electromagnetic coils 20 to the person sitting in seat 12 per the suggested treatment plan corresponding to the selected suggested treatment option 36.

Biometric sensor 34 is also in communication with controller 26 to provide a suggested treatment plan to the controller. When controller 26 is so configured, the controller automatically controls current generator 24 to provide the appropriate electrical currents to selected ones of electromagnetic coils 20 thereby causing electromagnetic energy to be delivered from these electromagnetic coils to the person sitting in seat 12 per the suggested treatment plan.

In embodiments, biometric sensor 34 is one or more of an electromyography (EMG) sensor, an oxygen sensor, a pressure sensor, and the like. In embodiments, the biomedical/biometrical systems of seating system 10 include an array of biometric sensors disposed in seat 12. The distribution of biometric sensors in seat 12 corresponds to the distribution of electromagnetic coils 20 or at least corresponds to major anatomical areas (thighs, buttocks, lumbar, thoracic cervical, etc.) of the person sitting in seat 12. When the person sitting in seat 12 experiences pain, the EMG pattern of the specific painful area changes from the normal baseline. Oxygen level as detected by the oxygen sensors in that area tends to decrease. Pain induced by pressure would be mitigated by the application of electromagnetic energy from neighboring electromagnetic coils 20.

Further in regards to automatic suggestion of electromagnetic coils 20 and electromagnetic field characteristics settings for consideration by the user and/or automatic selection of the electromagnetic coils and electromagnetic field characteristics settings, seating system 10 further includes a fidgeting sensor system (not shown) installed in seat 12 and/or in/around the vehicle. Sensor-based inputs from the fidgeting sensor system to GUI 30 are used for the automatic suggestion of electromagnetic coils 20 and electromagnetic field characteristics settings. Likewise, the sensor-based inputs from the fidgeting sensor system directly to controller 26 are used for the automatic selection suggestion of electromagnetic coils 20 and electromagnetic field characteristics settings.

Fidget sensor 38 shown in FIG. 2 represents the sensor(s) providing the sensor-based inputs from the fidgeting sensor system of seating system 10. Fidget sensor 38 is configured to detect the location of fidgeting of a person sitting in seat 12 and intuitively suggest one or more treatment options. The treatment options are to address the person's discomfort and/or pain which has manifested into the fidgeting. Fidget sensor 38 may be embodied as a piezo-electric sensor, a radar sensor, a Doppler based sensor, a piezo-resistive sensor, a capacitive sensor, a pressure-based sensor, a camera that visually detects fidgeting, and the like.

Fidget sensor 38 is in communication with GUI 30 to provide the suggested treatment plans to the GUI. GUI 30 in turn displays suggested treatment options 40 corresponding to the suggested treatment plans for the person to view. Upon the person selecting one of the suggested treatment options 40, controller 26 controls current generator 24 to provide the appropriate electrical currents to selected ones of electromagnetic coils 20 thereby causing electromagnetic energy to be delivered from these electromagnetic coils to the person sitting in seat 12 per the suggested treatment plan corresponding to the selected treatment option 40.

Fidget sensor 38 is also in communication with controller 26 to provide a suggested treatment plan to the controller. When controller 26 is so configured, the controller automatically controls current generator 24 to provide the appropriate electrical currents to selected ones of electromagnetic coils 20 thereby causing electromagnetic energy to be delivered from these electromagnetic coils to the person sitting in seat 12 per the suggested treatment plan.

Fidget sensor 38 may be the best manner to detect discomfort of the person sitting in seat 12 with current technology available. In embodiments, for the fidget detection, along with the other sensor types (capacitive, Doppler, etc.), fidget sensor 38 is a piezo or pressure-based sensor. In embodiments, the fidgeting sensor system of seating system 10 includes an array or map of fidget sensors disposed in seat 12. The distribution of fidget sensors in seat 12 corresponds to the distribution of electromagnetic coils 20 or at least corresponds to major anatomical areas (thighs, buttocks, lumbar, thoracic cervical, etc.) of the person sitting in the seat.

The person sitting in seat 12 in a state of comfort is relatively quiet. When pain/discomfort develops, the person starts exhibiting fidgeting. Fidgeting is a series of voluntary and involuntary movements that can have a specific repetitive pattern (typically, the area experiencing the most pain tends to move away to reduce the amount of pressure on to it). By looking at the presence of repetitive fidgets it can be determined whether the person is in a state of discomfort. It can be determined from analyzing the specific pattern what area of the person is most likely to hurt.

As described, seating system 10 through the various ways of selecting electromagnetic coils 20 for activation and electromagnetic field characteristics settings can create a custom profile for a person sitting in seat 12 who suffers from pain or discomfort. The pain or discomfort may be the result from a pre-existing condition and/or the result of a prolonged stay in the vehicle. In either case, electromagnetic coils 20 are controlled per the custom profile to provide therapeutic electromagnetic energy to the person sitting in seat 12 to alleviate or reduce the person's pain or discomfort.

As described, electromagnetic coils 20, which are powered individually, can be individually selected manually by the person sitting in the seat or automatically based on the output of biometric sensor 34 or fidget sensor 38 which detect pain, discomfort, fidgeting, and the like. As an example of electromagnetic coils 20 being individually selectable, the selected electromagnetic coils 20 could include two electromagnetic coils 20 located in the lumbar area of seat back 16, one electromagnetic coil 20 located in the left shoulder area of seat back 16, one electromagnetic coil 20 located in the proximity of the neck area of seat back 16, etc.

As described, seat 12 has a fixed N-size array of electromagnetic coils 20 adjustable to any seat style and surface. Electromagnetic coils 20 may be integrated into sub-components (including, but not limited to, trim or foam) of seat 12 or free-form existing between the trim and the seat foam. Additionally, the array of electromagnetic coils 20 could be designed as an independent structure added to seat 12. As indicated in FIGS. 1, 2, and 3, electromagnetic coils 20 interconnect via a main controller switch (i.e., controller 26 and current generator 24 in conjunction with one another) which regulates power and distribution. The switch is controlled by manual or automatic input.

As noted, electromagnetic coils 20 may be embodied via various types of electromagnetic energy generation systems. One or more of the various types of electromagnetic energy generation systems are integrated in seat 12 as electromagnetic coils 20 in such a manner to provide localized distribution of multiple nodes of independent electromagnetic energy capabilities. Selected electromagnetic coils 20 receive (selected) electrical currents supplied from current generator 24. These electromagnetic coils 20 generate electromagnetic energy in response to receiving the electrical currents. The electromagnetic energy is emitted from these electromagnetic coils 20 through the seating surface materials to be passed into the soft tissue of the person sitting in seat 12. Electromagnetic coils 20 are strategically distributed in seat 12 to allow for electromagnetic energy delivery targeting of major muscle groups over a variety of human types.

Electromagnetic energy from electromagnetic coils 20 passing into the person sitting in seat 12 may provide the following advantages: a comfortable environment for the person; reduce distraction of the person caused by pain and fatigue; improve, if possible, a standard of living of the person and like persons sitting in like vehicle seats; and offer pain relief in non-pharmaceutical and non-invasive ways.

Figure 4:
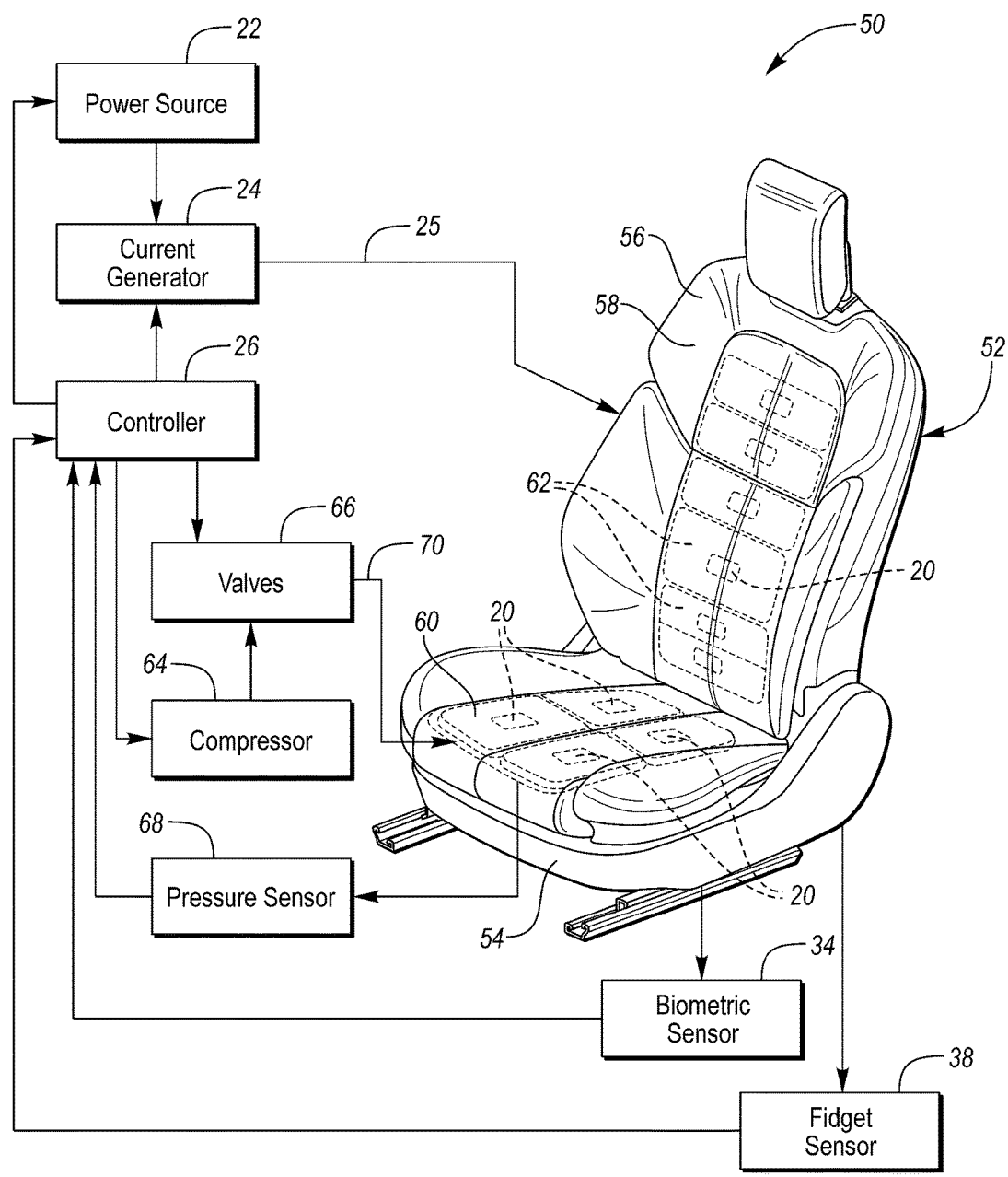
FIG. 4 illustrates a perspective view of another seating system for a vehicle including a perspective view of a vehicle seat of this seating system and a block diagram of other components of this seating system.

Referring now to FIG. 4, with continual reference to FIGS. 1, 2, and 3, another vehicle seating system 50 will be described. Vehicle seating system 10 includes a seat 52. A perspective view of seat 12 is shown in FIG. 1. Seat 52 includes a seat bottom 54 and a seat back 56 and a cover 58 which covers or upholsters the seat bottom and the seat back.

As shown in phantom in FIG. 4, seat 52 includes a set of air bladders 60 disposed in seat bottom 54 and a set of air bladders 62 disposed in seat back 56. Bladders 60 and 62 are inflatable and inflatable. This is exemplary as seat bottom 54 and seat back 56 may have none or one or more bladders. Further, the illustration in FIG. 4 is exemplary as bladders may be disposed at any locations of seat bottom 54 and seat back 56.

Seat 52 further includes an array of electromagnetic coils 20. At least some of electromagnetic coils 20 are respectively positioned in front of the "A-side" of at least some of bladders 60 and 62. Accordingly, as an air bladder and inflates to apply pressure to an affected area of a person sitting in seat 52 or to assist with postural change, the associated electromagnetic coil 20 is pushed forward against the person's body. This allows for better contact with electromagnetic coil 20 and more effective electromagnetic energy transfer. At least some of electromagnetic coils 20 may be respectively positioned back of the "B-side" of at least some of bladders 60 and 62.

The components of seating system 50 include power source 22, current generator 24, and controller 26. As described, current generator 25 provides electrical currents to electromagnetic coils 20 and the electromagnetic coils emit electromagnetic energy in response to receiving the electrical currents. Controller 26 controls current generator 24 to individually regulate electrical currents from the current generator to electromagnetic coils 20.

The components of seating system 50 further include a compressor 64, a plurality of valves 66, and a pressure sensor 68. Compressor 64 provides a source of air for inflating bladders 60 and 62. Valves 66 receive the compressed air from compressor 64. Valves 66 are in fluid communication respectively with bladders 60 and 62 via respective air tubes (generally indicated by reference numeral 70). Each bladder is fluidly connected by a respective air tube 70 to receive compressed air from compressor 64 via a respective valve 66. Air tubes 70 may be configured as flexible tubes, hoses, or the like. Controller 26 controls valves 66 to regulate the air into and out of bladders 60 and 62. In this way, bladders 60 and 62 are each adjustable and can be individually or collectively inflated and deflated.

Pressure sensor 68 is configured to detect the air pressure in one or more of bladders. 60 and 62. Controller 26 uses the value of the air pressure detected by pressure sensor 68 in controlling bladders 60 and 62 to inflate and deflate to targeted air pressures. In this way, controller 26 may control the inflating and deflating of bladders 60 and 62 in any of a plurality of predetermined or user-defined massage cycles to massage a person sitting in seat 52.

In embodiments, seat 52 may further include pneumatic pistons for stronger pressure points. Controller 26 is operable to individually control the pneumatic pistons in providing the pressure points. In this way, controller 26 may control the pneumatic pistons in any of the predetermined or user-defined massage cycles to massage a person sitting in seat 52.

Controller 26 is further in communication with biometric sensor 34 and fidget sensor 38. Controller 26 can inflate and deflate any of bladders 60 and 62 in response to either a biometric/biomedical input received from biometric sensor 34 or a fidgeting input received from fidget sensor 38 (i.e., through a fidgeting detection system, EMG-based device, localized oxygen level detection, pressure mapping device, or a combination thereof). In conjunction, controller 26 can control the electromagnetic field generation of electromagnetic coils 20 positioned on the bladders being inflated and deflated. In this way, the affected areas of a person sitting in seat 52 are sensed by biometric sensor 34 or fidget sensor 38 and controller 26 in turn reacts by inflating the corresponding bladders and initiating electromagnetic energy delivery.

As described, intended benefits of seating system 10 and seating system 50 include treating and preventing discomfort of the person sitting in seat 12. The discomfort can range from several sources including long distance driving, age of the person, pre-existing injuries or illnesses, and repetitive strain injuries. Additionally, as the electromagnetic energy is non-invasive, pharmaceutical side effects are not a consideration.

While exemplary embodiments are described above, it is not intended that these embodiments describe all possible forms of the present invention. Rather, the words used in the specification are words of description rather than limitation, and it is understood that various changes may be made without departing from the spirit and scope of the present invention. Additionally, the features of various implementing embodiments may be combined to form further embodiments of the present invention.

What is claimed is:

1. A seating system for a vehicle, comprising:
a vehicle seat;
a plurality of individually selectable and controllable electromagnetic coils individually positioned at respective locations within the seat corresponding to anatomical locations of a person sitting in the vehicle seat, the electromagnetic coils to generate electromagnetic fields when activated;
a plurality of air bladders disposed within the vehicle seat;
at least some of the electromagnetic coils are respectively positioned against at least some of the bladders; and
a controller to individually activate a subset of the electromagnetic coils to deliver electromagnetic energy to the anatomical locations of the person corresponding to the respective locations within the vehicle seat of the activated electromagnetic coils.

2. The seating system of claim 1 further comprising:
a human-machine interface to receive from the person a selection of the electromagnetic coils to activate; and
the controller to individually activate the electromagnetic coils selected by the person.

3. The seating system of claim 1 further comprising:
a biometric sensor to detect locations of discomfort of the person; and
the controller to individually activate the electromagnetic coils in accordance with a suggested treatment plan based on the detected locations of discomfort of the person.

4. The seating system of claim 3 wherein:
the biometric sensor includes at least one of a EMG-based device, a localized oxygen level detector, and a pressure detector.

5. The seating system of claim 1 further comprising:
a fidget sensor to detect locations of fidgeting of the person; and
the controller to individually activate the electromagnetic coils in accordance with a suggested treatment plan based on the detected locations of fidgeting of the person.

6. The seating system of claim 5 wherein:
the fidget sensor includes at least one of a piezo-electric sensor, a radar sensor, a Doppler based sensor, a piezo-resistive sensor, a capacitive sensor, a pressure-based sensor, and a camera.

7. The seating system of claim 1 wherein:
the electromagnetic coils include sewn conductive fibers.

8. The seating system of claim 1 wherein:
the electromagnetic coils are integrated into sub-components of the vehicle seat.

9. The seating system of claim 1 wherein:
the electromagnetic coils are between trim components and foam components of the vehicle seat.

10. The seating system of claim 1 wherein:
the electromagnetic coils are part of an independent structure separately removable from the seat.

11. The seating system of claim 1 further comprising:
a current generator to generate electrical currents; and
the controller to control electrical currents supplied from the current generator to the subset of the electromagnetic coils to individually activate the subset of the electromagnetic coils.

12. The seating system of claim 1 wherein:
the controller to control inflating and deflating of the air bladders having the activated electromagnetic coils positioned thereon in conjunction with activating the activated electromagnetic coils.

13. A seating system for a vehicle, comprising:
a vehicle seat;
a current generator to generate electrical currents;
a plurality of individually selectable and controllable electromagnetic coils individually positioned at respective locations within the vehicle seat corresponding to anatomical locations of a person sitting in the vehicle seat, the electromagnetic coils to generate electromagnetic fields having characteristics in correspondence with characteristics of electrical currents supplied to the electromagnetic coils;
a plurality of air bladders disposed within the vehicle seat;
at least some of the electromagnetic coils are respectively positioned against at least some of the bladders;
a controller to individually activate a subset of the electromagnetic coils and control electrical currents supplied from the current generator to the activated electromagnetic coils for the activated electromagnetic coils to deliver electromagnetic energy in correspondence with the electrical currents to the anatomical locations of the person corresponding to the respective locations within the vehicle seat of the activated electromagnetic coils; and
the controller to control inflating and deflating of the bladders having the activated electromagnetic coils positioned thereon in conjunction with activating the activated electromagnetic coils and controlling the electrical currents supplied from the current generator to the activated electromagnetic coils.

14. The seating system of claim 13 further comprising:
a human-machine interface; and
the controller is programmed with one or more treatment plans each having unique electromagnetic coil activation and electromagnetic field characteristics settings;
the human-machine interface to receive from the person a selection of one of the treatment plans; and
the controller to individually activate the electromagnetic coils and control the electrical currents supplied from the current generator to the activated electromagnetic coils in accordance with the selected treatment plan.

15. The seating system of claim 13 further comprising:
a biometric sensor to detect locations of discomfort of the person; and
the controller to individually activate the electromagnetic coils and control the electrical currents supplied from the current generator to the activated electromagnetic coils in accordance with a suggested treatment plan based on the detected locations of discomfort of the person.

16. The seating system of claim 13 further comprising:
a fidget sensor to detect locations of fidgeting of the person; and
the controller to individually activate the electromagnetic coils and control the electrical currents supplied from the current generator to the activated electromagnetic coils in accordance with a suggested treatment plan based on the detected locations of fidgeting of the person.

17. The seating system of claim 13 further comprising:
a biometric sensor to detect locations of discomfort of the person; and
the controller to individually activate the electromagnetic coils, control the electrical currents supplied from the current generator to the activated electromagnetic coils, and control inflating and deflating of the bladders having the activated electromagnetic coils positioned thereon in accordance with a suggested treatment plan based on the detected locations of discomfort of the person.

18. The seating system of claim 13 further comprising:
a fidget sensor to detect locations of fidgeting of the person; and
the controller to individually activate the electromagnetic coils, control the electrical currents supplied from the current generator to the activated electromagnetic coils, and control inflating and deflating of the bladders having the activated electromagnetic coils positioned thereon in accordance with a suggested treatment plan based on the detected locations of fidgeting of the person.

* * * * *